United States Patent [19]

DuBois et al.

[11] Patent Number: 4,618,487

[45] Date of Patent: Oct. 21, 1986

[54] DEVICE FOR ADMINISTERING CALCIUM ASCORBATE

[75] Inventors: Mark DuBois, Mt. View; Felix Theeuwes, Los Altos; Patrick S. L. Wong, Hayward, all of Calif.

[73] Assignee: ALZA Corporation, Palo Alto, Calif.

[21] Appl. No.: 764,027

[22] Filed: Aug. 9, 1985

Related U.S. Application Data

[63] Continuation-in-part of Ser. No. 628,677, Jul. 6, 1984, abandoned.

[51] Int. Cl.[4] .................. A61K 9/22; A61K 9/32; A61K 31/365
[52] U.S. Cl. .................................. 424/15; 514/474; 604/890; 604/892
[58] Field of Search .................. 424/15; 514/474; 604/890, 892

[56] References Cited

U.S. PATENT DOCUMENTS

| | | | |
|---|---|---|---|
| 2,348,503 | 5/1944 | Taylor | 514/474 |
| 3,697,641 | 10/1972 | Ahrens | 514/474 |
| 3,854,480 | 12/1974 | Zaffaroni | 604/892 |
| 3,944,064 | 3/1976 | Bashaw et al. | 424/14 |
| 4,036,948 | 7/1977 | Kitamori et al. | 514/474 |
| 4,203,442 | 5/1980 | Michaels | 604/892 |
| 4,203,997 | 5/1980 | Kuppers et al. | 514/474 |
| 4,439,196 | 3/1984 | Higuchi | 604/890 |
| 4,449,983 | 5/1984 | Cortese et al. | 604/892 |
| 4,519,801 | 5/1985 | Edgren | 604/890 |
| 4,522,625 | 6/1985 | Edgren | 604/890 |

*Primary Examiner*—Ronald W. Griffin
*Attorney, Agent, or Firm*—Paul L. Sabatine; Edward L. Mandell; Steven F. Stone

[57] ABSTRACT

A dispensing device is disclosed for delivering calcium ascorbate to a biological environment of use over time.

8 Claims, 4 Drawing Figures

DEVICE FOR ADMINISTERING CALCIUM ASCORBATE

CROSS-REFERENCE TO RELATED APPLICATIONS

This application is a continuation-in-part of U.S. application Ser. No. 06/628,677 filed on July 6, 1984, now abandoned.

FIELD OF THE INVENTION

This invention pertains to calcium ascorbate. More particularly, the invention relates to both a novel and useful delivery device for administering calcium ascorbate.

BACKGROUND OF THE INVENTION

It has long been recognized in the arts of medicine and pharmacy that vitamin C active agent is essential for good health. A vitamin C active agent is essential for the normal regulation of inter-cellular collagen, for the regulation of colloidal conditions of inter-cellular substances including the fibrils of connective tissues, and for healing bone fractures. A vitamin C active substance also is indicated as functioning in the metabolism of tyrosine, and it facilitates the absorption of iron. A deficiency of a vitamin C active agent results in a clinical breakdown of tissue structure, inter-cellular collagen substances, capillary defects, and the eventual development of scurvy. Scurvy has been known since the Middle Ages and it was found widespread in Northern Europe among the crews of sailing ships.

The daily intake of a vitamin C active agent is an absolute necessity for animals requiring exogenous vitamin C active substance. Usually some of the needed vitamin C active agent can be provided in the dietary intake. There are, however, instances where all of the vitamin C active agent must be provided from a non-dietary source, and there are numerous instances where additional or supplemental vitamin C active agent must be provided for satisfying the daily requirements, or for satisfying the increased requirements associated with clinical conditions. For example, vitamin C active agent requirements are increased during pregnancy and lactating periods, following trauma, during infections, for wound healing, for shortening the illness period, and for alleviating the symptoms associated with the common cold.

It has long been recognized also in the arts of medicine and pharmacy that calcium is the most abundant cation in the animal body. In the body, calcium serves as the principal component of skeletal tissues. The calcium ion influences blood coagulation, neuromuscular excitability, cellular adhesiveness, nerve impulse transmission, maintenance and function of cell membranes, activation of enzyme reactions, and hormone secretion. The daily intake of calcium is necessary to replace calcium in the skeleton. The skeleton functions in many instants as a reservoir of calcium and it is in a dynamic equilibrium with circulating calcium. The calcium moiety in the blood is a physiologically important factor for regulating membrane transport enzyme activity and hormonal secretion. Daily calcium intake is necessary for the vital functions of the animal body. Additionally, calcium requirements are increased during periods of active skeletal growth and pregnancy. Also, calcium ingestation in larger amounts is indicated in ulcer patients.

It will be appreciated, in the light of the above presentation, by those versed in the arts to which this invention pertains, that a critical need exists for a delivery device for delivering a vitamin C active agent and calcium, such as calcium ascorbate, to a host in need of same. The need exists for a controlled release delivery device that can deliver calcium ascorbate for satisfying part of the daily requirement, for satisfying all of the daily requirement, or for supplementing the requirement associated with an increased demand for vitamin C and calcium as satisfied by the administration of calcium ascorbate. The need exists for a delivery device that can deliver, at a controlled rate, calcium ascorbate as the primary exogenous source of vitamin C and calcium over a prolonged period of time.

OBJECTS OF THE INVENTION

Accordingly, in view of the above presentation, it is an immediate object of this invention to provide a device for delivering calcium ascorbate to produce a beneficial effect and for substantially satisfying the demands associated with the prior art.

Another object of the present invention is to provide a novel delivery device that delivers calcium ascorbate and maintains its delivery continuously over a controlled time release period.

Another object of the present invention is to provide a delivery device that operates osmotically and can deliver calcium ascorbate independent of the pH of the environment over a prolonged period of time.

Another object of the present invention is to provide a delivery device that can deliver calcium ascorbate to an environment of use and which delivery device maintains its physical and chemical integrity during the delivery of calcium ascorbate in the environment of use.

Another object of the present invention is to provide a delivery device that substantially reduces, and/or substantially eliminates the unwanted influence of an environment of use on calcium ascorbate by storing and protecting calcium ascorbate against the deleterious effects of the environment until its release from the device.

Another object of the invention is to provide an osmotic delivery device for oral admittance into the gastrointestinal tract for administering calcium ascorbate therein as it travels the length of the tract.

Another object of the invention is to provide a dispensing device comprising calcium ascorbate for administering to the gastrointestinal tract with less irritation of the gastromucosal tissues.

Another object of the present invention is to provide a dispensing device comprising calcium ascorbate for administering to a biological environment accompanied by a substantial decrease in the incident of irritation associated with other forms of vitamin C.

Another object of the invention is to provide a dispensing device that delivers calcium ascorbate to animals requiring both exogenous vitamin C and calcium that are essential for biological processes and nutrition, thereby aiding in fulfilling these therapeutically essential needs.

Another object of the present invention is to provide a dispensing device for delivering calcium ascorbate that delivers the calcium ascorbate and substantially collapses at the end of the delivery period.

Other objects, features and advantages of the invention will be more apparent to those skilled in the art from the detailed description of the specification, taken in conjunction with the drawings and the accompanying claims.

DETAILED DESCRIPTION OF THE DRAWINGS

In the drawings, which are not drawn to scale, but are set forth to illustrate various embodiments of the invention, the drawing figures appear as follows.

In the drawings and in the specification, like parts in related figures are identified by like numbers. The terms appearing earlier in the specification and in the description of the drawings, as well as embodiment thereof, are detailed in the disclosure.

DETAILED DESCRIPTION OF THE DRAWINGS

The present invention provides a delivery device for dispensing the vitamin calcium ascorbate. The expression calcium ascorbate as used herein comprises anhydrous calcium ascorbate and dihydrate calcium ascorbate. The vitamin, in both instances, comprises 2 moles of ascorbic acid and 1 mole of calcium, that when administered to a host, produces simultaneously a vitamin C and a calcium beneficial therapeutic effect.

Figure 1:
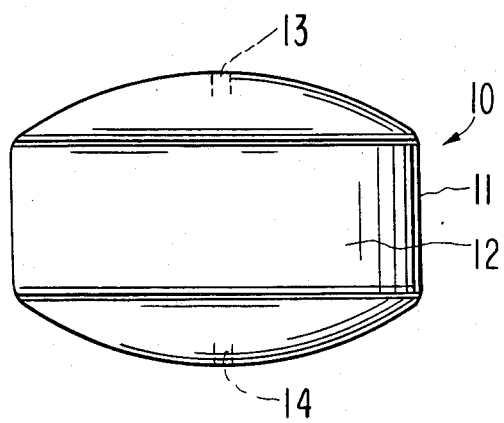
FIG. 1 is a view of the therapeutic delivery system designed for orally delivering the presently preferred vitamin calcium ascorbate.

In accordance with the practice of this invention, a delivery device for dispensing calcium ascorbate to a biological environment of use is depicted in FIG. 1. In FIG. 1, delivery device 10 is seen comprising a body member 11 having a wall 12 that surrounds and forms an internal compartment, not seen in FIG. 1. Device 10 comprises at least one passageway 13 and in an optional embodiment device 10 comprises a second passageway 14. The passageways 13 and 14 are illustrated on opposite faced surfaces of device 10; however, in another embodiment passageway 13 and passageway 14 can be on adjacent surfaces of device 10.

Figure 2:
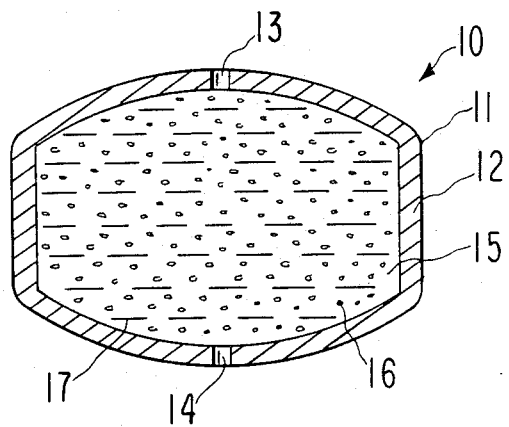
FIG. 2 is an opened view of the delivery system of FIG. 1 for illustrating the structure of the delivery device.

In FIG. 2, device 10 of FIG. 1 is seen in opened section. In FIG. 2, delivery device 10 comprises body 11 formed of wall 12 that surrounds and defines an internal compartment 15. A pair of prepositioned passageways, passageway 13 and passageway 14, connects compartment 15 with the exterior of device 10. Compartment 15 houses beneficial calcium ascorbate 16. In operation compartment 15 contains calcium ascorbate 16 and a fluid 17. Fluid 17 is imbibed into compartment 15 through wall 12 during operation of device 10, when device 10 is in a biological fluid environment of use. Wall 12 is formed of a polymeric material that is substantially permeable to the passage of an external fluid and it is substantially impermeable to the passage of beneficial agent. The polymeric composition comprising wall 12 is nontoxic, inert, and it maintains its physical and chemical integrity during the delivery period of calcium ascorbate from device 10.

Figure 3:
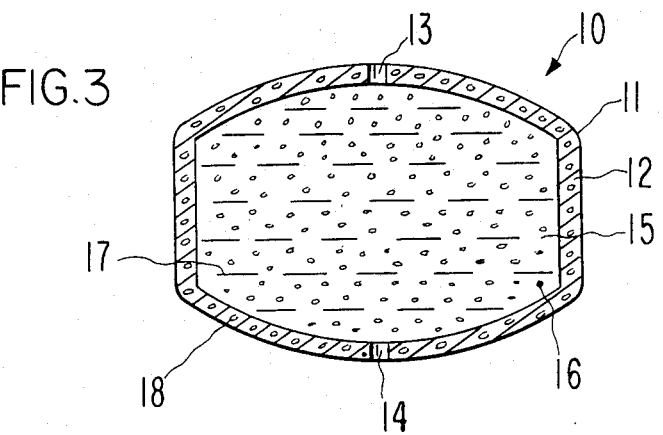
FIG. 3 is an opened view of the delivery device of FIG. 1 for depicting the device in operation administering the calcium ascorbate active agent.

In FIG. 3, device 10 of FIG. 1 is seen in opened section. In FIG. 3, delivery device 10 comprises body 11 formed of wall 12 that surrounds and forms internal compartment 15. Device 10 comprises a first passageway 13 and a second passageway 14 spaced apart in wall 12. In a presently preferred manufacture, passageway 13 and passageway 14 are positioned on opposite sides of device 10. In this latter manufacture, passageway 13 and passageway 14 are positioned on distant facing surfaces of device 10 with compartment 15 interdisposed between passageway 13 and passageway 14. In another manufacture, the passageways can be located on adjacent surfaces of device 10. Compartment 15 of FIG. 3 initially contains beneficial vitamin calcium ascorbate 16, and subsequently during operation of device 10 a fluid 17 that is present in the environment of use and is imbibed through wall 12 into compartment 15. Wall 12 of device 10 of FIG. 3 comprises a polymeric composition that is substantially permeable to the passage of external fluid 17. Wall 12 additionally contains a compound that is soluble in an aqueous fluid and in fluid present in the environment of use. The fluid soluble compound acts as a flux enhancer for letting fluid 17 enter compartment 15, which compound on being dissolved or leached from wall 12 forms a micropore 18 fluid path. Compartment 15 optionally can contain cysteine that functions as an added stabilizer for prolonging the shelf-life of the dispensing system.

Figure 4:
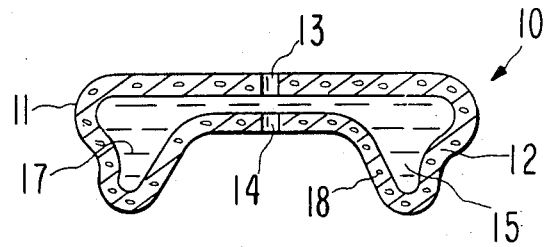
FIG. 4 is an opened view depicting the delivery device at the end of the delivery period.

Device 10, when in operation in the environment of use, delivers calcium ascorbate 16 by two distinct operations. In operation (1), device 10 releases calcium ascorbate 16 by fluid 17 being imbibed through semipermeable wall 12 into compartment 15. In compartment 15, the imbibed fluid 17 continuously dissolves and forms a solution of calcium ascorbate that is osmotically and hydrodynamically delivered through a single passageway 13, through a pair of passageways 13 and 14, or through a multiplicity of passageways from device 10 to the environment of use. In operation (2), device 10 releases calcium ascorbate 16 by the combined operations of (a), fluid 17 permeating through wall 12 into compartment 15, and (b), fluid dissolving or leaching the fluid soluble compound from wall 12 for forming micropores 18 in wall 12. The combined or dual operations occur simultaneously during the delivery period. In these operations, calcium ascorbate 16 is hydrodynamically pumped through passageways 13 and 14, and some calcium ascorbate 16 diffuses through micropores 18 now filled with fluid to the exterior of device 10. Delivery device 10 as seen in FIG. 4 is illustrated at the end of the delivery period. Device 10 delivers calcium ascorbate 16 until the end of the delivery period. At the end of the period, device 10 substantially collapses as seen in FIG. 4, with a small volume of fluid 17 and a trace amount of calcium ascorbate remaining in compartment 15.

DETAILED DESCRIPTION OF THE INVENTION

Wall 12 of delivery device 10 is formed of a material that does not adversely affect calcium ascorbate 16, an animal or other host. Wall 12 in one embodiment comprises a selectively semipermeable material that maintains its physical and chemical integrity in the environment of use. The phrase, maintains it physical and chemical integrity, denotes, as presently used herein, the wall does not erode and it does not dissolve in the environment of use. One material useful for forming wall 12 is the semipermeable polymer cellulose acylate, and more particularly cellulose acetate. In a presently preferred embodiment, the cellulose acetate has an acetyl content of 20% to 44%. In another embodiment another material useful for forming wall 12 of device 10 is cellulose ether. Generally, the cellulose ether has an ethoxy content of 15% to 80%, with the presently preferred cellulose ether having an ethoxy content of from 30% to 50%. A typical cellulose ether is ethylcellulose having an ethoxy content of 40% to 50%, and the like. Wall 12 of device 10 generally is about 0.5 mils to 15 mils thick (12.7×10$^{-3}$ mm to 381×10$^{-3}$ mm), and the like.

Wall 12 of delivery device 10 also can comprise a flux enhancing agent. The presently preferred flux enhancer is a non-toxic ethylene glycol polymer that is soluble in fluid present in the environment of use. The ethylene glycol polymers are characterized by the general formulae $HOCH_2(CH_2OCH_2)_mCH_2OH$, wherein m is 5 to 36; and $H(OCH_2CH_2)_mOH$, wherein m is 8 to 84. Specific ethylene glycol polymers include a member selected from the group consisting of $OCH_2(CH_2OCH_2)_mCH_2OH$, wherein m is 5 to 5.75; $HOCH_2(CH_2OCH_2)_mCH_2OH$, wherein m is 8.2 to 9.1; and $H(OCH_2CH_2)_mOH$ wherein m is 68 to 84. These ethylene glycol polymers are available as polyethylene glycol 300, polyethylene glycol 400, polyethylene glycol 1540 and polyethylene glycol 3350. The polyethylene glycol flux enhancers generally have a molecular weight of 300 to 4200. Additional flux enhancer that can be present in wall 12 include sorbitol that is leached from wall 12 and hydroxypropyl methylcellulose having a viscosity of 6 CPS. The flux enhancer, when device 10 is in operation in the fluid environment of use, permits external fluid to permeate into compartment 15 of device 10, and on its being dissolved or leached in situ from wall 12 forms a multiplicity of micropores 18 in wall 12. Further in operation, micropores 18 fill with external fluid and form a plurality of diffusional paths for the diffusion of calcium ascorbate active agent 16 from compartment 15 through the flux enhancer vacated micropores. The amount of flux enhancer in wall 12 generally is from 5% to 50% by weight.

The expression, "passageway" as used herein comprises means and methods suitable for releasing calcium ascorbate from the compartment. The passageway or orifice will pass through the wall for communicating with the compartment. The expression, "passageway" includes aperature, orifice, bore, pore, porous element through which a beneficial agent can migrate, hollow fiber, capillary tube, and the like. The expression also includes a material that erodes in the environment of use to produce a passageway in the device. Representative materials suitable for forming a passageway include an erodible poly(glycol) and poly(lactic) acid in the wall, gelatinous filaments, poly(vinyl alcohol), and the like. The passageway can be formed by leaching a material such as sorbitol, poly(glycol), and the like, from the he wall. The passageway can have any shape. For example, round, triangular, square, elliptical, irregular, and the like. The expression, "osmotic passageway" includes passageways formed by mechanical drilling or laser drilling through the wall. Generally for the purposes of this invention, the passageway will have a maximum cross-sectional area, A, defined by equation 1:

$$L/F \times Qv/t \times 1/DS \tag{1}$$

wherein L is the length of the passageway, (Qv/t) is the mass delivery rate of the agent released per unit of time, D is the diffusion coefficient of the medicine in the release solution, S is the solubility of the medicine in the fluid, and F has a value of approximately 1 to 1000, said osmotic passageway having a minimum area, $A_s$, defined by equation 2:

$$\left[ \frac{Lv}{t} \times 8 \times \frac{\pi \eta}{\Delta P} \right]^{\frac{1}{2}} \tag{2}$$

wherein L is the length of the passageway, v/t is the volume of the medicine released per unit of time, $\pi$ is 3.14, $\eta$ is the viscosity of the solution being released, and $\Delta P$ is the hydrostatic pressure difference between the inside and the outside of the compartment and having a value up to 20 ATM. The dimension for the osmotic passageway is disclosed in U.S. Pat. No. 3,916,899. Laser drilling equipment having photo detection means for orienting a device for surface selected drilling are known in U.S. Pat. Nos. 4,063,064 and 4,088,864. Dispenser 10 has at least one exit passageway formed in operation, or preformed during manufacture of dispenser 10. Dispenser 10 optionally comprises more than one passageway, which are an exit means in wall 12 for dispensing calcium ascorbate from dispenser 10.

The amount of calcium ascorbate 16 present in compartment 15 of device 10 generally is about 0.05 ng to 10 g, with individual devices containing, for example, 25 ng, 5 mg, 50 mg, 100 mg, 250 mg, 500 mg, 750 mg, 1.0 g, 1.250 g, and the like. Generally when compartment 15 comprises calcium ascorbate anhydrous, each 100 mg of calcium ascorbate will comprise 10.3% calcium and 89.7% ascorbic acid, and when compartment 15 comprises calcium ascorbate dihydrate, each 100 mg of calcium ascorbate dihydrate will comprise 9.40% calcium and 90.6% ascorbic acid and water. Representative examples of device 10 include a device comprising 385 mg of calcium ascorbate dihydrate correspondingly containing 318 mg of vitamin C and 36 mg of calcium available as the salt, a device comprising 687 mg of calcium ascorbate dihydrate containing 568 mg of vitamin C and 65 mg of calcium. The devices can be administered orally once, twice, thrice daily, or the like. The device can be administered one at an administration, two at an administration, and the like. The devices can be taken daily, weekly, monthly and over like prolonged periods of time.

Device 10 is manufactured by standard manufacturing techniques. In one embodiment, calcium ascorbate and other reservoir forming ingredients that are housed in compartment 15 are blended and pressed into a solid possessing a shape and dimensions that correspond to the shape and dimensions of compartment 15 of device 10. The compartment forming ingredients and, optionally, a solvent are mixed into a solid formed by conventional methods such as ballmilling, calendering, stirring, or rollmilling, and then pressed into a preselected shape. Next, wall 12 is applied around compartment 15 forming ingredients. Wall 12 can be applied by molding, pan coating, spraying, or dipping the pressed shapes into a wall forming composition. Another, and presently preferred technique that can be used for applying wall 12 is the air suspension procedure. This procedure consists of suspending and tumbling pressed agent 16 in a current of air and wall forming composition until the wall is applied to pressed agent 16. The air suspension procedure is described in U.S. Pat. No. 2,779,241; *J. Am. Pharm. Assoc.*, Vol. 48, pp 451–459, 1979, and, ibid, Vol. 49, pp 82–84, 1960. Other coating procedures that can be used include airless pressurized spray such as the Hi-coater the Glatt coater, and the like.

Exemplary solvents suitable for manufacturing the wall include inorganic and organic solvents that do not adversely harm the wall forming materials and the final device. The solvents include members selected from the group consisting of aqueous solvents, alcohols, ketones, esters, ethers, aliphatic hydrocarbons, halogenated solvents, cycloaliphatic, aromatic, heterocyclic solvents, and mixtures thereof. Typical solvents include acetone, diacetone alcohol, ethanol, ethanol, isopropyl alcohol, butyl alcohol, methyl acetate, ethyl acetate, n-butyl acetate, methyl isobutyl ketone, methyl propyl ketone, n-hexane, n-heptane, methylene chloride, ethylene chloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water and mixtures thereof such as acetone and water, acetone and methanol, acetone and ethyl alcohol, methylene dichloride and methanol, ethylene dichloride and methanol, and the like.

DESCRIPTION OF EXAMPLES

The following examples are merely illustrative of the present invention, and they should not be considered as limiting the scope of the invention in any way. The examples of the invention, and other equivalents thereof, will become apparent to those versed in the art in the light of the present disclosure, the drawings and the accompanying claims.

EXAMPLE 1

A therapeutic device for the controlled and continuous oral administration of beneficial vitamin calcium ascorbate is made as follows: First, a compartment forming composition weighing 532.50 mg and containing 500 mg of anhydrous calcium ascorbate is made as follows: 500 mg of calcium ascorbate, 26.6 mg of polyvinyl pyrrolidone and 5.9 mg of magnesium stearate are thoroughly mixed and pressed in a Manesty press with a 7/16 inch round punch using a pressure head of 1½ tons to produce a drug composition.

Next, a semipermeable wall is formed by blending 27.2 mg of cellulose acetate having an acetyl content of 39.8%, 8.8 mg of sorbitol and 4.0 mg of polyethylene glycol 400 and spray coating with a solvent consisting of 714 ml of acetone and 186 ml of water in an air suspension machine until a semipermeable wall surrounds the compartment. The coated device was dried for 72 hours at 50° C. and then a 0.26 mm orifice was hand drilled into the wall. The osmotic dispensing device can be administered once a day or more often for administering vitamin C and calcium for good health.

EXAMPLE 2

A delivery device for the continuous administration of calcium ascorbate in the gastrointestinal tract is prepared as follows: First, a compartment forming composition weighing 1068.90 mg and consisting essentially of 94% anhydrous calcium ascorbate, 5% polyvinyl pyrrolidone and 1% of magnesium stearate are mixed thoroughly and pressed in a Manesty press with a ¾ oval inch punch using a pressure head of three tons.

Next, a semipermeable wall weighing 26 mg is coated around the calcium ascorbate composition. The wall is formed from a composition comprising 75% cellulose acetate having an acetyl content of 39.8%, 15% sorbitol and 10% polyethylene glycol 400. The coating is effected from a coating solvent consisting of 500 ml of acetone and 130 ml of water in an air suspension machine. The coated device is dried for 15 hours at 50° C. and an orifice having a diameter of 0.26 mm is hand drilled into the wall. The device had a wall thickness of 5.1 mils and releases calcium ascorbate over a prolonged period of time.

EXAMPLE 3

A delivery device for the controlled and continuous delivery of calcium ascorbate is made as follows: A compartment forming composition weighing 1219 mg and consisting essentially of 79% calcium ascorbate; 20% polyethylene oxide having a molecular weight of 600,000 and available as Polyox ®205, and 1% magnesium stearate are mixed thoroughly and pressed in a Manesty press with a ¾ inch oval punch under a pressure of three tons.

Next, a wall weighing 20 mg is applied around the vitamin composition. The wall is formed from a composition consisting essentially of 82% cellulose acetate having an acetyl content of 39.8%, 9% hydroxypropyl methylcellulose having a viscosity of 6 centipoises and 9% polyethylene glycol 3350. The wall is coated using a mixed solvent consisting of 580 ml of methylene chloride and 83 ml of methanol. The coated devices are dried for 55 hours at 50° C. Four orifices of 20 mils diameter are drilled through the wall.

EXAMPLE 4

A delivery device for the controlled and the continuous delivery of calcium ascorbate is prepared as follows: A composition weighing 1060.70 mg and consisting essentially of 94% calcium ascorbate, 5% polyvinyl pyrrolidone and 1% magnesium stearate is prepared by thoroughly and homogeneously blending the ingredients into a unit mass. The blended composition is pressed in a ¾ inch oval punch under a pressure head of three tons.

Next, a wall is applied around the pressed solid composition. The wall weighed 36 mg and consists essentially of 55% ethylcellulose having an ethoxy content of 49.5%, 30% sorbitol and 15% polyethylene glycol 3350. The wall is coated using a mixed solvent consisting of 700 ml of methylene chloride and 300 ml of methanol. The wall coated device is dried for 15 hours at 55° C. The device forms exit releasing means in the form of controlled porosity passageways in operation in the environment of use.

EXAMPLE 5

A delivery device for the controlled and the continuous delivery of calcium ascorbate over time to a warm-blooded animal including a human is prepared according to the procedure of Example 4. In this example the compartment of the device comprises 1138.5 mg of calcium ascorbate, 49.5 mg of microcrystalline cellulose commercially available as Avicel ®PH-102, 2.5 mg of magnesium stearate and 12.7 mg of stearic acid. The wall comprises 25.5 mg of ethylcellulose having an ethoxy content of 49.5% and 10.5 mg of polyethylene glycol 3350.

EXAMPLE 6

The procedure of Example 4 is followed with the delivery device produced by the instant example comprising a compartment weight of 1214.9 mg, which comprises 94.5% calcium ascorbate, 0.8% silicon dioxide, 0.5% cystein, 2.5% stearic acid and 1.7% magnesium stearate. The wall of the device comprises 55% ethylcellulose having an ethoxy content of 49.5% and 45% polyethylene glycol 3350. The device has 2 passageways on distant facing surfaces.

EXAMPLE 7

A dispensing device for the controlled administration of calcium ascorbate was prepared according to the above procedures. The compartment of the device comprised 708 mg of calcium ascorbate. The compartment on a weight percent basis contained 92.5 wt percent calcium ascorbate, 5 wt percent polyvinyl pyrrolidone, 2 wt percent magnesium stearate and 0.5 wt percent Acdisol ®, an internally cross-linked form of sodium carboxymethyl cellulose. The wall of the device comprised 84 wt percent cellulose acetate having an acetyl content of 39.8%, 12 wt percent polyethylene glycol 3350, and 4 wt percent hydroxypropyl methylcellulose having a viscosity of 6 centipoises. The device has two ten mil passageways. The device exhibits a release rate for $t_{450}$ mg over 17 hours or 26.5 mg/hr. The device provides vitamin C for the therapies indicated above, and calcium for physiological functional integrity of tissues, for normal cardiac function, for use in the coagulation of blood, for maintaining the structural contiguity of cells and for bone maintenance. The physiology of vitamin C and calcium are presented in *The Pharmacological Basis of Therapeutics,* 4th Ed., by Goodman and Gilman, 1970, published by MacMillan Co., London.

EXAMPLE 8

The procedure set forth in Example 7 is followed in the present example. The device provided by this example contains 346 mg of calcium ascorbate dihydrate and provides 32 mg of calcium. The compartment of the device also contains 18.9 mg of polyvinyl pyrrolidone, 7.5 mg of magnesium stearate, and 1.9 mg of Acdisol ®. The semipermeable wall comprises 9.1 mg of cellulose acetate having an acetyl content of 39.8%, 0.6 mg of polyethylene glycol 3350, and 0.21 mg of hydroxypropyl methylcellulose. The device exhibits a $t_{225}$ mg over 14.3 hours at 15.7 mg/hr. The device has two ten mil passageways on one face of the device.

EXAMPLE 9

The procedure set forth in Example 7 is followed in the present example. In the present example the device comprises 330.5 mg of calcium ascorbate dihydrate providing 31 mg of calcium. The compartment of the device also contains 18.1 mg of polyvinyl pyrrolidone, 7.2 mg of magnesium stearate, and 1.8 mg of Acdisol ®. The semipermeable wall comprises 8.7 mg of cellulose acetate having an acetyl content of 39.8%, 0.61 mg of polyethylene glycol 3350 and 0.2 mg of hydroxypropyl methylcellulose. The device has two ten mil passageways on opposite surfaces and releases 13.9 mg/hr. over a period of 16.2 hours.

EXAMPLE 10

A dispensing device for administering calcium ascorbate is prepared according to the above examples. The device of this example comprises a 745.90 mg composition consisting of 92.50% calcium ascorbate, 5% polyvinyl pyrrolidone, 2% magnesium stearate and 0.5% cross-linked sodium carboxymethyl cellulose. The wall of the device weighed 10 mg and it comprises 84% cellulose acetate having an acetyl content of 39.8%, 12% polyethylene glycol 3350, and 4% hydroxypropyl methylcellulose. The device has two 10 mil passageways on a single face. The final calcium ascorbate content of the device is 575.50 mg. The device releases 511.8 mg in 24 hrs., for an average rate of release of 21.3 mg/hr.

EXAMPLE 11

A dispensing device for delivering calcium ascorbate is prepared according to the above examples. The device of this example comprises a 722.60 composition in its reservoir comprising 92.50% calcium ascorbate dihydrate, 5% polyvinyl pyrrolidone, 2% magnesium stearate, and 0.5% cross-linked sodium carboxymethyl cellulose. The wall of the device weighed 18.8 mg and it comprises 84% cellulose acetate having an acetyl content of 39.8%, 12.0% polyethylene glycol 3350, and 4% hydroxypropyl methylcellulose. The device has two 0.26 mm passageways, an average rate of release of 25.7 mg/hr., with a 96% cumulative amount released over 21 hrs.

EXAMPLES 12–14

A series of dispensing devices are prepared wherein the device comprises: (a) 589.20 mg of calcium ascorbate released at an average rate of release of 22.3 mg/hr. over 24 hrs.; a device comprising 556.60 mg of calcium ascorbate released at an average rate of release of 26.8 mg/hr. for 24 hrs.; and a device comprising 574.40 mg of calcium ascorbate released at a release rate of 26.4 mg/hr. over a prolonged period of 24 hrs.

The novel device and the calcium ascorbate delivered by the device are administered substantially free of tissue irritation. The presence or the absence of tissue irritation for a drug including a vitamin can be ascertained with a known test. One test for irritation consists of using rabbits that are anesthetized. Their colon is exposed through a mid-line abdominal incision and a segment is isolated by placing 2 sets of 2 ligatures ≦ 20 cm apart around the colon and cutting in between each set. The isolated segment is cut longitudinally, distal to the blood vessels and nerves which continue to supply the segment. The isolated segment is clamped in a multi-chambered cell and each cell perfused with artificial intestinal fluid at 37° C. Delivery devices dispensing calcium ascorbate or vitamin C are placed in the cells directly into contact with the mucosal tissue for a period of at least three hours. Tissue irritations in response to the test calcium ascorbate and the vitamin C, (ascorbic acid), ascertained at the end of the test leading to an irritation index. Procedures for measuring irritation are known in *J. Pharm. Sci.,* Vol. 60, No. 9, pp 1314–1316, 1971; *Arzneim-Forsch Drug Res.,* Vol. 23, No. 12, pp 1709–1712, 1973; and in *Laryngoscope,* Vol. 93, pp 184–187, 1985. The irritation study classifies irritation on a scale of 0 to 5, and includes erythema, wrinkling, blanching and ulceration, where zero signified zero irritation, one to two signifies mild irritation, two-three signifies moderate irritation, three to four signifies severe irritation, and above five signifies very severe irritation. The results of the above irritation study indicated that calcium ascorbate produced an irritation index of zero irritation, and that vitamin C produced an irritation index of five. The comparison tests indicate the unobvious and unexpected results obtained by the delivery device delivering calcium ascorbate according to the mode and manner of the invention. The novel devices embody delivery means for the obtainment of precise delivery rates in the environment of use, while simultaneously maintaining the integrity and physical character of the delivery device. While there has been described and pointed out features of the invention as applied to presently preferred embodiments, those skilled in the subject art will appreciate that various modifications, changes, additions and omissions in the delivery device illustrated and described can be made without departing from the spirit of the invention.

We claim:

1. A dispensing device for the rate controlled delivery of the beneficial agent calcium ascorbate to a biological environment of use, said dispensing device comprising:
   (a) a wall comprising a member selected from the group consisting of a cellulose acylate and cellulose ether, which wall permits the passage of fluid present in the biological environment of use and maintains its physical and chemical integrity in the presence of calcium ascorbate, which wall also surrounds and defines:
   (b) a compartment;
   (c) a beneficially effective amount of calcium ascorbate in the compartment;
   (d) means in the wall communicating with the compartment and the exterior of the dispensing device for delivering the calcium ascorbate to the biological environment of use; and,
   (e) wherein, when the dispensing device is in operation in the biological environment of use, the dispensing device delivers the calcium ascorbate to the biological environment with a substantial decrease in irritation of the tissues of the biological environment.

2. The dispensing device for the rate controlled delivery of the beneficial agent calcium ascorbate according to claim 1, wherein the biological environment of use is the gastrointestinal tract of a human and the dispensing device is shaped and adapted for oral admittance into the environment of use.

3. The dispensing device for the rate controlled delivery of the beneficial agent calcium ascorbate according to claim 1, wherein the means in the wall for delivering calcium ascorbate are formed when the dispensing device is in the environment of use.

4. The dispensing device for the rate controlled delivery of the beneficial agent calcium ascorbate according to claim 1, wherein the means in the wall for delivering calcium ascorbate comprises at least one passageway.

5. The dispensing device for the rate controlled delivery of the beneficial agent calcium ascorbate according to claim 1, wherein when the device is in operation in the environment of use, the device hydroxynamically pumps calcium ascorbate through the means in the wall to the environment of use.

6. The dispensing device for the rate controlled delivery of the beneficial agent calcium ascorbate according to claim 1, wherein the compartment comprises from 1 mg to 1500 mg of calcium ascorbate.

7. The dispensing device for the rate controlled delivery of the beneficial agent calcium ascorbate according to claim 1, wherein said compartment comprises 100 mg to 750 mg of calcium ascorbate that is delivered through the means in the wall thereby providing calcium and vitamin C with substantially less tissue irritation than associated with vitamin C alone.

8. A dispensing device for the rate controlled delivery of use beneficial agent calcium ascorbate to a biological environment of use, said dispensing device comprising:
   (a) a wall comprising a member selected from the group consisting of a cellulose acylate and cellulose ether, which wall permits the passage of fluid present in the biological environment of use and maintains its physical and chemical integrity in the presence of calcium ascorbate, said wall surrounding and defining:
   (b) a compartment;
   (c) a composition of matter in the compartment, which composition comprises from 1 mg to 1500 mg of the following members: 75% to 95% calcium ascorbate, 0% to 5% polyvinyl pyrrolidone, 0% to 5% magnesium stearate, 0% to 5% stearic acid, 0% to 5% sodium carboxymethylcellulose, and 0% to 5% silicon dioxide, with the total percentage of all members 100;
   (d) means in the wall communicating with the compartment and the exterior of the dispensing device for delivering the calcium ascorbate to the biological environment of use; and,
   (e) wherein, when the dispensing device is in operation in the biological environment of use, the dispensing device delivers the calcium ascorbate to the biological environment of use.

* * * * *